United States Patent
Lind

(10) Patent No.: US 8,372,086 B2
(45) Date of Patent: Feb. 12, 2013

(54) SKIN CARE FILE AND METHOD

(76) Inventor: Lesley Lind, Tampa, FL (US)

(*) Notice: Subject to any disclaimer, the term of this patent is extended or adjusted under 35 U.S.C. 154(b) by 2011 days.

(21) Appl. No.: 11/167,360

(22) Filed: Jun. 27, 2005

(65) Prior Publication Data

US 2005/0216034 A1 Sep. 29, 2005

Related U.S. Application Data

(60) Provisional application No. 60/600,019, filed on Aug. 9, 2004.

(51) Int. Cl.
*A61B 17/50* (2006.01)

(52) U.S. Cl. ............... 606/131; 132/75.6; 132/76.5

(58) Field of Classification Search .......... 606/131, 606/133; 132/75.6, 76.4, 76.5; D28/59
See application file for complete search history.

(56) References Cited

U.S. PATENT DOCUMENTS

| | | |
|---|---|---|
| 180,501 A | 8/1876 | Sodadee |
| 291,460 A | 1/1884 | Yeatman |
| 306,298 A | 10/1884 | Walling |
| 454,436 A | 6/1891 | Hesse |
| 2,308,624 A | 1/1943 | Pauech |
| D155,773 S | 11/1949 | Becker |
| 3,141,270 A | 7/1964 | Ferrand |
| 3,369,283 A | 2/1968 | Colding |
| 3,956,858 A | 5/1976 | Catlin et al. |
| 4,018,576 A | 4/1977 | Lowder et al. |
| 5,088,509 A * | 2/1992 | Savage, III ........... 132/76.5 |
| 5,317,839 A | 6/1994 | Anderson |
| D364,226 S | 11/1995 | Hartmann |
| D369,658 S * | 5/1996 | Holt ................. D24/147 |
| D388,616 S * | 1/1998 | Wieder et al. ........... D4/111 |
| 5,732,719 A | 3/1998 | Godbout |
| D412,764 S | 8/1999 | Godbout |
| 5,997,549 A | 12/1999 | Sauceda et al. |
| 6,015,293 A * | 1/2000 | Rimkus ............... 433/141 |
| D431,096 S | 9/2000 | Rieser |
| D442,741 S | 5/2001 | Rieser |
| 6,283,978 B1 | 9/2001 | Cheski et al. |
| 6,308,416 B1 * | 10/2001 | Bosy et al. ............ 30/50 |
| 6,363,944 B1 * | 4/2002 | Stangenberg ............ 132/76.4 |
| D460,186 S | 7/2002 | Park |
| D460,554 S | 7/2002 | Park |
| D461,246 S | 8/2002 | Park |
| 6,625,839 B2 * | 9/2003 | Fischer et al. ........... 15/160 |
| D480,511 S | 10/2003 | Rosie et al. |
| D486,607 S | 2/2004 | Chien |
| D496,731 S | 9/2004 | Park |
| 6,811,477 B2 | 11/2004 | Funakubo |
| D532,933 S * | 11/2006 | Choi ................. D28/59 |
| 2001/0018061 A1 * | 8/2001 | Rhoades ............. 424/401 |
| 2004/0092959 A1 * | 5/2004 | Bernaz .............. 606/131 |
| 2005/0033316 A1 * | 2/2005 | Kertz .............. 606/131 |
| 2007/0208354 A1 * | 9/2007 | Barraclough et al. ...... 606/133 |
| 2007/0244491 A1 * | 10/2007 | Russell ............. 606/131 |

* cited by examiner

*Primary Examiner* — S. Thomas Hughes
*Assistant Examiner* — Julie A Szpira
(74) *Attorney, Agent, or Firm* — Andrew F. Knight

(57) ABSTRACT

A skin care file includes a substantially linear handle portion, a substantially rounded file portion having an edge, and a substantially linear arm portion connecting the handle portion to the file portion. An angle between the handle portion and the arm portion is between approximately 15° and 60°. The file portion has a maximum dimension between approximately 0.5 and 1.5 inches. The file portion includes on at least one side and on at least a portion of the edge a grit surface having a grit between approximately 120 and 60 grit.

20 Claims, 2 Drawing Sheets

SKIN CARE FILE AND METHOD

CROSS REFERENCE TO RELATED APPLICATIONS

The present application claims priority to U.S. Provisional Application No. 60/600,019, filed Aug. 9, 2004, entitled "Skin Resurfacing Tool and Method."

BACKGROUND

In the field of skincare, dermatology, and aesthestics, the need often arises to remove layers of a patient's skin. There is a need for a tool and method for quickly, efficiently, cost effectively, safely, controlledly exfoliating a patient's epidermis.

SUMMARY OF THE INVENTION

According to an embodiment, a skin care file comprises: a substantially linear handle portion; a substantially rounded file portion having an edge; and a substantially linear arm portion connecting the handle portion to the file portion, wherein an angle between the handle portion and the arm portion is between approximately 15° and 60°, wherein the file portion has a maximum dimension between approximately 0.5 and 1.5 inches, and wherein the file portion comprises on at least one side and on at least a portion of the edge a grit surface having a grit between approximately 120 and 60 grit.

In one aspect, the grit surface is integrally formed with the file portion. In one aspect, the grit surface comprises granules coated on the file portion. In one aspect, the granules comprise diamonds.

In one aspect, the arm portion is connected to the handle portion via a hinged joint, whereby the angle is adjustable. In one aspect, the handle portion is flexible, whereby a pressure of the file portion against skin corresponds to a flexure of the handle portion. In one aspect, the handle portion is substantially inflexible. The handle portion may comprise steel, for example.

In one aspect, the file portion comprises an edge, and a portion of the edge that is substantially less than a whole of the edge comprises the integrally formed grit surface. In one aspect, the file portion comprises an edge, substantially a whole of the edge comprises the integrally formed grit surface, and the handle portion does not comprise the integrally formed grit surface.

In one aspect, the maximum dimension is between approximately 0.7 and 1.0 inches. In one aspect, the file portion is substantially flat and circular. In one aspect, the at least one side of the file portion is substantially convex.

According to an embodiment, a skin care file comprises: a handle portion; and a file portion connected to the handle portion, wherein the file portion has a maximum dimension between approximately 0.5 and 1.5 inches, and wherein the file portion comprises on at least one side an integrally formed grit surface having a grit between approximately 120 and 60 grit.

In one aspect, the skin care file further comprises an arm portion connecting the handle portion to the file portion, wherein the handle portion and arm portion are each substantially linear, and wherein an angle between the handle portion and arm portion is between approximately 15° and 60°.

In one aspect, the arm portion is connected to the handle portion via a hinged joint, whereby the angle is adjustable. In one aspect, the handle portion is flexible, whereby a pressure of the file portion against skin corresponds to a flexure of the handle portion.

In one aspect, the file portion comprises an edge, and a portion of the edge that is substantially less than a whole of the edge comprises the integrally formed grit surface. In one aspect, the file portion comprises an edge, substantially a whole of the edge comprises the integrally formed grit surface, and the handle portion does not comprise the integrally formed grit surface.

In one aspect, the maximum dimension is between approximately 0.7 and 1.0 inches. In one aspect, the file portion is substantially flat and circular. In one aspect, the at least one side of the file portion is substantially convex.

According to an embodiment, a method of exfoliating skin from a person's face comprises: a) providing the skin care file as in any of the disclosed embodiments or aspects; and b) filing at least a portion of the person's face by applying the file portion of the skin care file to the person's face and moving the file relative to the person's face. In one aspect, the method further comprises: before step a), cleaning the person's face and drying the person's face; and after step b), cleaning the person's face and applying a lotion to hydrate the person's face.

According to an embodiment, a method of exfoliating skin from a person's face comprises: cleaning the person's face; drying the person's face; providing a skin care file comprising a handle portion and a file portion connected to the handle portion, wherein the file portion has a maximum dimension between approximately 0.5 and 1.5 inches; filing at least a portion of the person's face by applying the file portion of the skin care file to the person's face and cyclically moving the file; cleaning the person's face; and applying a lotion to hydrate the person's face.

In one aspect, the grit surface is integrally formed with the file portion. In one aspect, the grit surface comprises granules coated on the file portion. In one aspect, the granules comprise diamonds.

In one aspect, the file portion comprises on at least one side a grit surface having a grit between approximately 120 and 60 grit.

In one aspect, the skin care file further comprises an arm portion connecting the handle portion to the file portion, wherein the handle portion and arm portion are each substantially linear, and wherein an angle between the handle portion and arm portion is between approximately 15° and 60°.

In one aspect, the arm portion is connected to the handle portion via a hinged joint, whereby the angle is adjustable. In one aspect, the handle portion is flexible, whereby a pressure of the file portion against skin corresponds to a flexure of the handle portion.

In one aspect, the file portion comprises an edge, and a portion of the edge that is substantially less than a whole of the edge comprises the integrally formed grit surface. In one aspect, the file portion comprises an edge, substantially a whole of the edge comprises the integrally formed grit surface, and the handle portion does not comprise the integrally formed grit surface.

In one aspect, the maximum dimension is between approximately 0.7 and 1.0 inches. In one aspect, the file portion is substantially flat and circular. In one aspect, the at least one side of the file portion is substantially convex.

DETAILED DESCRIPTION

In the following description, the use of "a," "an," or "the" can refer to the plural. All examples given are for clarification only, and are not intended to limit the scope of the invention.

Figure 1:
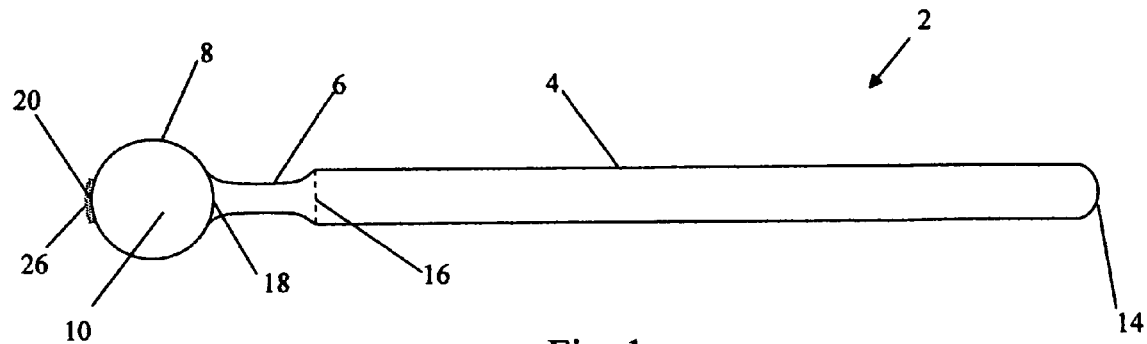
FIG. 1 shows a top view of a skin care file according to one embodiment.
Figure 2:
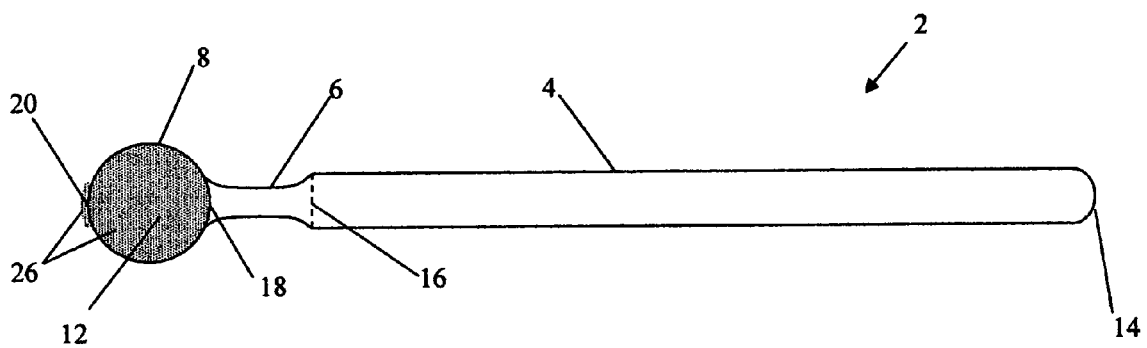
FIG. 2 shows a bottom view of the skin care file shown in FIG. 1.
Figure 3:
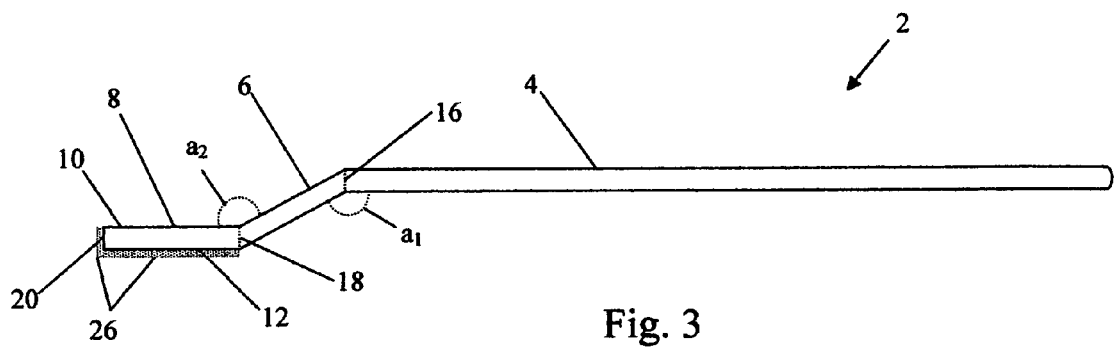
FIG. 3 shows a side view of the skin care file shown in FIG. 1.

Referring now to FIGS. 1-3, the Perfect Appearance™ skin care file tool 2 (also known as a skin resurfacing tool and/or Dermafile™) is preferably made of any hard, strong material, such as plastic or wood, preferably a highly polished material (e.g., metal) such as aluminum, steel or stainless steel. The tool 2 comprises a handle portion 4, an arm portion 6, and a file portion 8. The handle portion is configured to be held by a human hand so as to manipulate the file portion. The handle portion 4 may include a grip, such as a contoured region corresponding to one or more fingers, and/or a high-friction material (such as rubber, plastic, and so forth) to prevent the sliding of the tool 2 in the human hand. The handle portion 4 may have a rough surface in at least some parts to prevent sliding of the tool 2 from the user's hands. The handle portion 4 may include a rounded end portion 14. The handle portion 4 may have a substantially flat shape, similar to a Popsicle™ stick or medical tongue depressor, or may have a round shape, such as a pencil, or any other shape known in the art. The handle portion 4 may have a thickness of between approximately 1/16" and 3/8", preferably between approximately 1/8" and 1/4", preferably around 1/8". The handle portion 4 may have a length of between approximately 3" and 8", preferably between approximately 4" and 6", preferably about 5" or 6". Alternatively or in addition, at least one of the arm portion 6 and the handle portion 4 may be at least somewhat flexible, so that the pressure of the file portion 8 on the patient's skin may be adjusted by adjusting the flexure of the arm portion 6 and/or handle portion 4. The arm portion 6 and/or handle portion 4 may instead be substantially inflexible, and may comprise a stiff material, such as a hard plastic, metal (e.g., steel), or ceramic. Each of the arm portion 6 and handle portion 4 may be substantially linear, but may also or alternatively be contoured or bent, such as to contour to the shape of a human hand.

The tool 2 has a skin smoothing file portion 8 which may comprise an upper surface 10 which may be smooth and/or polished (e.g., which may be similar to the handle portion 4 in smoothness, if the handle portion 4 is smooth), and a lower surface 12 which may serve as the filing region. The lower surface 12 comprises a grit surface 26 that is gritty and rough to allow the user to rub the lower surface 12 against a patient's skin and file/sand/exfoliate that patient's skin. The grit surface 26 may comprise and/or be coated with any substance known in the art of filing, such as finely granulated, very hard materials, such as finely crushed genuine diamonds, silicon dioxide, crystals, gems, metals, and so forth. Alternatively or in addition, the grit surface 26 need not comprise and/or be coated with a granulated material; rather, the surface 26 itself may be formed to be rough and "gritty" so as to allow the lower surface 12 to file. In other words, the grit surface 26 may be integrally formed with the lower surface 12. Methods for integrally forming a grit surface on a hard surface are known in the art.

This file portion 8 may come in several (diamond or other) grit file sizes, such as fine, medium, coarse, and extra coarse, as known by one of ordinary skill in the art. Preferably the grit of the grit surface 26 is in the range of approximately 120 grit to 60 grit, preferably 100 grit to 80 grit. Where the grit surface 26 is not integrally formed with the lower surface 12, the granulated filing material (if used) may be attached to the lower surface 12 of the file portion 8 by any known method known in the art, such as electroplating, glue, varieties of welding, and so forth.

Figure 6:
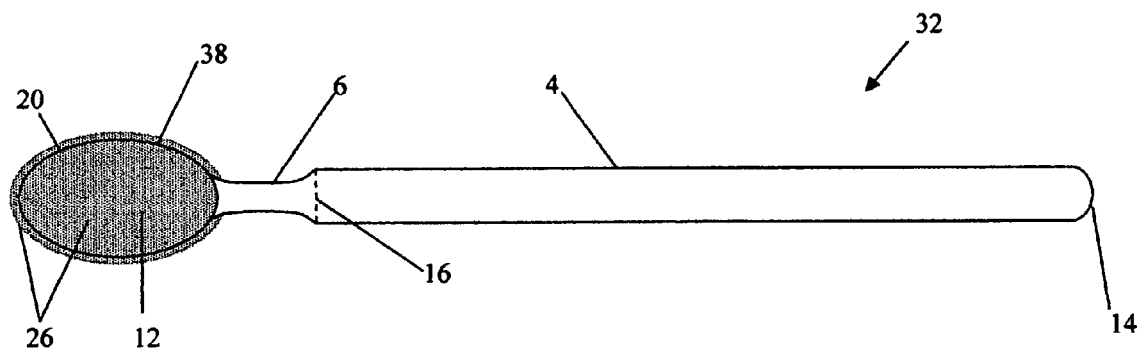
FIG. 6 shows a bottom view of a skin care file according to one embodiment.

Referring now to FIGS. 1 and 2, in one embodiment, the file portion 8 has a round cross sectional shape (the cross section taken from a top or bottom view, e.g., as in the bottom view shown in FIG. 2), such as circular, oval, elliptical, or any other shape, such as square, rectangular, triangular, diamond shaped, and so forth. Preferably, the file portion 8 has a round (preferably circular) diamond-surfaced shape that has a diameter (which is a maximum dimension in the case of a circle) between approximately 0.25 inches and 2.0 inches, preferably between approximately 0.5 inches and 1.5 inches, preferably between approximately 0.7 inches and 1.0 inches, and most preferably approximately 7/8". Of course, any range within the stated ranges is also within the scope of the present invention. Further, where the file portion 8 is not circular, a maximum dimension (e.g., the major axis in the case of a ellipsis, etc.) is preferably within the ranges stated. This size allows the file portion 8 to lie flat on the skin for even resurfacing. The tool 32 of FIG. 6 shows an example of a file portion 38 having a rounded but substantially oval or elliptical shape.

Figure 5:
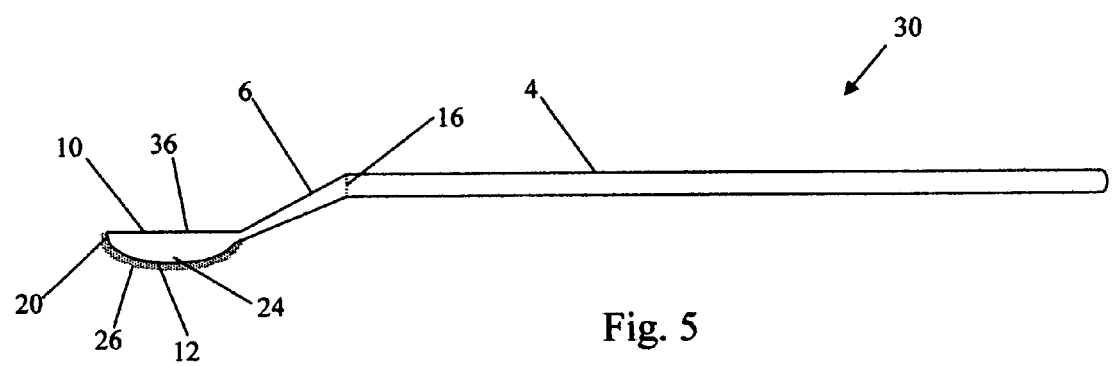
FIG. 5 shows a side view of a skin care file according to one embodiment.

Referring now to FIG. 3, in one embodiment, the file portion 8 may be substantially flat (e.g., having a rectangular cross sectional shape (the cross section taken from a side view, e.g., as in the side view shown in FIG. 3)), so that the file portion 8 lays substantially flat on a patient's face while using the tool 2. Alternatively, the file portion 8 may have a substantially convex or concave shape so that the mentioned cross section is round. In other words, a cross section showing a side view of the tool 2 would show the file portion 8 having a substantially round lower surface 12. For example, a tool 30 having a file portion 36 with a substantially convex region 24 of a substantially convex shape is shown in FIG. 5.

The file portion 8 may also include an edge 20 that may also act as a filing region, e.g., by being coated with one of the mentioned granulated materials (e.g., diamonds). In other words, the file portion 8 comprises on at least one side (e.g., the lower surface 12) and on at least a portion of the edge 20 the grit surface 26. Only a portion of the edge 20 (e.g., substantially less than a whole of the edge 20) comprises the grit surface 26 in one embodiment, while in another embodiment (such as that shown in FIG. 6), substantially a whole of the edge 20 comprises the grit surface 26. Further, the handle portion 4 and the arm portion 6 may not comprise the grit surface 26. Such a feature would allow the filing region 8 to fit in small areas for exfoliating skin from small or hard to reach areas.

The file portion 8 may be connected to the handle portion 4 via an arm portion 6. In one embodiment, the connection is integral. The arm portion 6 may be substantially flat and/or straight/linear, and may be connected to the handle portion 4 via a joint 16 (which may be integral), and to the file portion 8 via a joint 18 (which may be integral). Alternatively or in addition, the joints 16, 18 may be hinged, so that a first angle $a_1$ between the arm portion 6 and handle portion 4, and a second angle $a_2$ between the arm portion 6 and the file portion 8, may be adjusted. In one embodiment, the first angle $a_1$ is preferably between 0° and 60°, preferably between 15° and 45°, preferably between 25° and 35°, and preferably about 30°. In one embodiment, the second angle $a_2$ is preferably between 0° and 60°, preferably between 15° and 45°, preferably between 25° and 35°, and preferably about 30°. The joints 16, 18 may be sharp (as shown), or may be smoothed or rounded so that the angles are not so abrupt. The arm portion 6 may have a width equal to, smaller than, or larger than the width of the handle portion 4 (smaller than, as shown in FIG. 1), and preferably has a length of between about ¼" and 1", preferably approximately ½.

Figure 4:
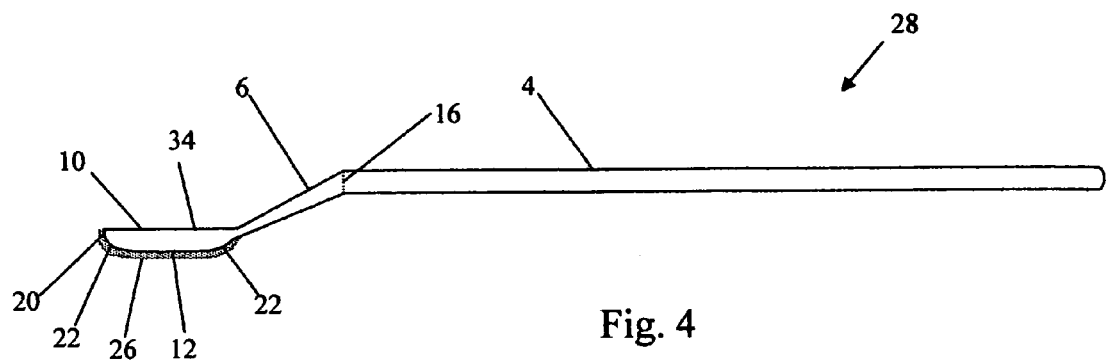
FIG. 4 shows a side view of a skin care file according to one embodiment.

Referring now to FIG. 4, a skin care file tool 28 differs from the tool 2 shown in FIG. 3 at least in that the file portion 34 comprises rounded regions 22 connecting the edge 20 to the lower surface 22. The lower surface and at least a portion of the edge 20 and rounded regions 22 comprise the grit surface 26. The file portion 34 retains a substantially flat and circular shape.

Referring now to FIG. 5, a skin care file tool 30 differs from the tool 2 shown in FIG. 3 at least in that the file portion 36 comprises a substantially convex region 24 so that the file portion 36 has a substantially convex cross section.

Referring now to FIG. 6, a skin care file tool 32 differs from the tool 2 shown in FIG. 2 at least in that the file portion 38 has a substantially oval or elliptical shape, and substantially a whole of the edge 20 comprises the grit surface 26.

The drawings are not necessarily to scale. For example, the grit surface 26 shown in the drawings may not be as thick as shown, and may comprise a very thin layer of granules or particles integrally formed or connected to the lower surface 12.

The Perfect Appearance™ skin care file tool 2 and method enables a user to file one's skin by hand, leaving smooth, fresh, rejuvenated skin. The technician has total control over the process, allowing varying levels of the epidermis to be safely removed. This tool may be used on any part of the body. It is a very effective tool for treating aging and sun damaged skin, acne scarring, pigmentation, stretch marks, fine lines and enlarged and clogged pores, by safely and effectively removing layers of the epidermis in a controlled, specific manner. Exfoliation further stimulates collagen production. The tool may also smooth rough calloused skin on elbows, knees and feet. This tool will complement any skin care regimen and can be used in place of chemical peeling and microdermabrasion. Results can very from a light polishing to gradual deep resurfacing.

With proper care this tool is designed to give a lifetime of consistent and effective treatments. The Perfect Appearance™ skin care file tool 2 may be cleaned with a soft brush and a disinfectant soap and water followed by cold sterilization or autoclaving.

In a method utilizing the above tool 2, a user identifies a specified region of a patient's skin (e.g., the patient's face) that should be exfoliated for better aesthetics and/or health. The user grips the tool 2 at the handle portion 4 and contacts a specified region of a patient's skin using the lower surface 12 (i.e., the filing region) of the file portion 8. The user uses a preferably circular or back-and-forth motion relative to the patient's skin to remove layers of the patient's skin from the specified region(s). For edges or hard-to-reach regions, the user may lift the tool 2 so that only the edge 20 contacts the skin, and may repeat the motion to remove skin from the region. The edge 20 may be limited to only one edge area of the file portion 8 (as in FIG. 2), such as an end or side edge, or may cover the entire edge area (not shown), such as the whole circumference of the round file portion 8. The user may adjust the pressure of the file portion 8 on the patient's skin by adjusting the flexure of the handle portion 4.

Further, the method may also include cleaning the person's face and drying the person's face before the filing or exfoliation procedure, and then subsequently cleaning the person's face and applying a lotion to hydrate the person's face.

Most of the embodiments described herein have represented simple versions for clarity of explanation. As understood by one of ordinary skill in the art, many of the features and/or aspects of the embodiments described herein may be "mixed and matched" to the extent physically possible to satisfy individual design requirements. As merely an example of such allowable mixing and matching, the feature in FIG. 6 showing that substantially a whole of the edge 20 comprises the grit surface 26 may be imported into the embodiment shown in FIG. 2, in which the file portion 8 has a substantially flat and circular shape. Further, the convex cross sectional shape of the file portion 36 of the tool 30 shown in FIG. 5 may be imported into the file portion 38 of the tool 32 shown in FIG. 6, and so forth.

These variations are merely examples, and do not limit the scope of the present invention. Any features described herein may be mixed and matched with other features to form embodiments not specifically described but within the scope of the present invention.

What is claimed is:

1. A skin care file, comprising:
    a substantially linear handle portion;
    a substantially rounded file portion having an edge; and
    a substantially linear arm portion connecting the handle portion to the file portion,
    wherein an angle between the handle portion and the arm portion is between approximately 15° and 60°,
    wherein the file portion has a maximum dimension between approximately 0.5 and 1.75 inches, and
    wherein the file portion comprises on at least one side and on at least a portion of the edge a grit surface having a grit between approximately 120 and 60 grit.

2. The skin care file as claimed in claim 1, wherein the arm portion is connected to the handle portion via a hinged joint, whereby the angle is adjustable.

3. The skin care file as claimed in claim 1, wherein the handle portion is flexible, whereby a pressure of the file portion against skin corresponds to a flexure of the handle portion.

4. The skin care file as claimed in claim 1, wherein substantially less than a whole of the edge comprises the grit surface.

5. The skin care file as claimed in claim 1, wherein substantially a whole of the edge comprises the grit surface, and wherein the handle portion does not comprise the grit surface.

6. The skin care file as claimed in claim 1, wherein the maximum dimension is between approximately 0.7 and 1.0 inches.

7. The skin care file as claimed in claim 1, wherein the file portion is substantially flat and circular.

8. The skin care file as claimed in claim 1, wherein the at least one side of the file portion is substantially convex.

9. A method of exfoliating skin from a person's face, comprising:
    a) providing the skin care file as claimed in claim 1; and
    b) filing at least a portion of the person's face by applying the file portion of the skin care file to the person's face and moving the file relative to the person's face.

10. A skin care file, comprising:
    a handle portion; and a file portion connected to the handle portion,
wherein the file portion has a maximum dimension between approximately 0.5 and 1.75 inches, and
wherein the file portion comprises on at least one side an integrally formed grit surface having a grit between approximately 120 and 60 grit.

11. The skin care tool as claimed in claim 10, further comprising an arm portion connecting the handle portion to the file portion, wherein the handle portion and arm portion are each substantially linear, and wherein an angle between the handle portion and arm portion is between approximately 15° and 60°.

12. The skin care file as claimed in claim 10, wherein the file portion comprises an edge, wherein substantially a whole of the edge comprises the integrally formed grit surface, and wherein the handle portion does not comprise the integrally formed grit surface.

13. The skin care file as claimed in claim 10, wherein the maximum dimension is between approximately 0.7 and 1.0 inches.

14. The skin care file as claimed in claim 10, wherein the file portion is substantially flat and circular.

15. A method of exfoliating skin from a person's face, comprising:
 a) providing the skin care file as claimed in claim 10; and
 b) filing at least a portion of the person's face by applying the file portion of the skin care file to the person's face and moving the file relative to the person's face.

16. A method of exfoliating skin from a person's face, comprising:
 cleaning the person's face;
 drying the person's face;
 providing a skin care file comprising a handle portion and a file portion connected to the handle portion, wherein the file portion comprises a grit surface and has a maximum dimension between approximately 0.5 and 1.75 inches;
 filing at least a portion of the person's face by applying the file portion of the skin care file to the person's face and cyclically moving the file;
 cleaning the person's face; and
 applying a lotion to hydrate the person's face,
 wherein the file portion comprises an edge, and
 wherein at least a portion of the edge comprises the grit surface.

17. The method as claimed in claim 16, further comprising an arm portion connecting the handle portion to the file portion, wherein the handle portion and arm portion are each substantially linear, and wherein an angle between the handle portion and arm portion is between approximately 15° and 60°.

18. The method as claimed in claim 16, wherein substantially a whole of the edge comprises the grit surface, and wherein the handle portion does not comprise the grit surface.

19. The method as claimed in claim 16, wherein the maximum dimension is between approximately 0.7 and 1.0 inches.

20. The method as claimed in claim 16, wherein the file portion is substantially flat and circular.

\* \* \* \* \*